(12) United States Patent
Liu et al.

(10) Patent No.: US 8,742,148 B1
(45) Date of Patent: Jun. 3, 2014

(54) OLIGOMERIZATION OF JOJOBA OIL IN SUPER-CRITICAL CO₂ FOR DIFFERENT APPLICATIONS

(75) Inventors: Zengshe Liu, Morton, IL (US); Shailesh N. Shah, Sugar-Land, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 325 days.

(21) Appl. No.: 13/237,072

(22) Filed: Sep. 20, 2011

Related U.S. Application Data

(60) Provisional application No. 61/387,619, filed on Sep. 29, 2010.

(51) Int. Cl.
  *C09F 7/06* (2006.01)
  *C07C 57/00* (2006.01)
  *C10M 105/36* (2006.01)

(52) U.S. Cl.
  USPC ............... 554/26; 554/228; 554/25; 554/28; 508/496

(58) Field of Classification Search
  None
  See application file for complete search history.

(56) References Cited

U.S. PATENT DOCUMENTS

| | | | |
|---|---|---|---|
| 2,260,417 A | 10/1941 | Whiteley et al. | |
| 2,922,763 A * | 1/1960 | Tierney | 508/251 |
| 6,281,373 B1 * | 8/2001 | Sato et al. | 554/167 |
| 7,691,946 B2 | 4/2010 | Liu et al. | |

OTHER PUBLICATIONS

Busson-Breysse, J., et al., "Jojoba Wax: Its Esters and Some of Its Minor Components", JAOCS, vol. 71, No. 9, Sep. 1994, pp. 999-1002.

Cowan, J. C., "Dimer Acids", The Journal of the American Oil Chemists Society, Dec. 1962, vol. 39, pp. 534-545.

Liu, Zengshe, et al., "From Oligomers to Molecular Giants of Soybean Oil in Supercritical Carbon Dioxide Medium: 1. Preparation of Polymers with Lower Molecular Weight From Soybean Oil", Biomacromolecules, 2007, vol. 8, pp. 233-239.

Miwa, Thomas K., "Jojoba Oil Wax Esters and Derived Fatty Acids and Alcohols: Gas Chromatographic Analyses", Journal of the American Oil Chemists "Society", vol. 48, Jun. 1971, pp. 259-264.

Shah, Shailesh, et al., "Preparation and Evaluation of Jojoba Oil Methyl Esters as Biodiesel and as a Blend Component in Ultra-Low Sulfur Diesel Fuel", Bioenerg. Res., 2010, vol. 3, pp. 214-223.

Miwa, Thomas K., "Structural Determination and Use of Jojoba Oil", JAOCS, vol. 61, No. 2, Feb. 1984, pp. 407-410.

Busson-Breysse, J. et al., "Jojoba Wax: Its Esters and Some of Its Minor Components", JAOCS, vol. 71, No. 9, Sep. 1994, pp. 999-1002.

Shah, Shailesh N. et al., "Preparation and Evacuation of Jojoba Oil Methyl Esters as Biodiesal and as a Blend Component Ultra-Low Sulfur Diesal Fuel", Bioenerg. Res., Spring Science + Media, LLC, 2009, Published Oct. 15, 2009.

\* cited by examiner

*Primary Examiner* — Yate K Cutliff
(74) *Attorney, Agent, or Firm* — John D. Fado; Howard Owens

(57) ABSTRACT

Dimers of jojoba oil wax esters are prepared by reacting the wax esters in the presence of a catalytically effective amount of an acid catalyst in supercritical $CO_2$. In the reaction, the double bonds of the wax esters are opened and cross link or polymerize two wax esters as dimers. The jojoba ester dimers which are produced are of the formula:

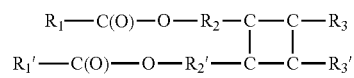

wherein $R_1$ and $R_1'$ are independently selected from the group consisting of C15-C23 monounsaturated hydrocarbons, $R_2$ and $R_2'$ are independently selected from the group consisting of C8-C14 saturated hydrocarbons, and $R_3$ and $R_3'$ are independently selected from the group consisting of C6-C8 saturated hydrocarbons.

18 Claims, No Drawings

OLIGOMERIZATION OF JOJOBA OIL IN SUPER-CRITICAL $CO_2$ FOR DIFFERENT APPLICATIONS

CROSS-REFERENCE TO RELATED APPLICATIONS

This application claims the benefit under 35 U.S.C. 1.19(e) of U.S. provisional 61/387,619 filed Sep. 29, 2010, the contents of which are incorporated by reference herein.

BACKGROUND OF THE INVENTION

1. Field of the Invention

The invention relates to novel oligomers of jojoba oil wax esters and a process for their preparation.

2. Description of the Prior Art

Jojoba (*Simmondsia chinensis*) is a perennial shrub that is native to the Mojave and Sonoran deserts of Arizona, California and western Mexico. Jojoba is also cultivated in certain hot, arid areas such as Israel, the Mediterranean, India, Africa and South America.

Unlike most other plants, the oil of jojoba seeds, which constitutes between 45-55%, by weight, of the seeds, is mainly composed of long chain monoesters of fatty acids and alcohols (97-98%, by weight) rather than triglycerides. These esters, which are commonly referred to as wax esters, are straight chain esters predominantly 36-46 carbons in length, with an ester approximately in the center of the chain. Sterols and free fatty acids and alcohols are present in substantially lower amounts, particularly in the oil from mature seeds.

The oil exists as a liquid at room temperature, and is used extensively in the cosmetic and pharmaceutical industries for its dermatological properties. The oil may also be used as a source of phytosterols. In crude oils, phytosterols exist as free sterols and as sterol esters, although sterol glycosides and acylated glycosides may also be present. Jojoba oil is also used as an alternative to sperm oil as a lubricant and as a plasticizer. Because it is not subject to lipase hydrolysis and is thus poorly digested, jojoba oil has also been investigated as a non-caloric fat replacement in foods.

SUMMARY OF THE INVENTION

We have now discovered novel dimers of jojoba oil wax esters and a process for their preparation. In this process, jojoba oil wax esters are reacted in the presence of a catalytically effective amount of an acid catalyst in supercritical $CO_2$. In the reaction, the double bonds of the wax esters are opened and cross link or polymerize two wax esters as dimers. The jojoba ester dimers which are produced are of the formula:

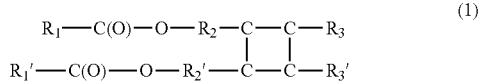

(1)

wherein R1 and R1' are independently selected from the group consisting of C15-C23 monounsaturated hydrocarbons, R2 and R2' are independently selected from the group consisting of C8-C14 saturated hydrocarbons, and R3 and R3' are independently selected from the group consisting of C6-C8 saturated hydrocarbons. Interestingly, the dimerized jojoba oil produced is a solid at room temperature, with a melting point approximately at human body temperature.

In accordance with this discovery, it is an object of this invention to provide novel dimers of jojoba oil wax esters and a process for their preparation.

Another object of this invention is to provide novel dimers from jojoba oil which are solids at room temperature and liquids near body temperature.

It is also an object of this invention to provide novel dimers from jojoba oil for use in cosmetic, pharmaceutical and/or dermatological products, or in lubricants or nanolubricatants, or as non-caloric fat-free food additives or plasticizers.

A further object of this invention is to provide a method for producing dimers from jojoba oil which is environmentally friendly without the use of organic solvents.

Other objects and advantages of this invention will become readily apparent from the ensuing description.

DETAILED DESCRIPTION OF THE INVENTION

The starting material for use in the invention is the oil (lipid fraction) from jojoba seeds, *Simmondsia chinensis*, which is available from a variety of commercial sources. Alternatively, the oil may be extracted from mature jojoba seed by conventional techniques such as cold pressing and/or solvent extraction. As described by Busson-Breysse et al (1994. Jojoba Wax: Its Esters and Some of Its Minor Components. JAOCS. 71:999-1002) and Miwa (1984. Structural Determination and Uses of Jojoba Oil. JAOCS. 61:407-410), the contents of each of which are incorporated by reference herein, the wax ester fraction of jojoba oil includes esters of a fatty acid (FA) with an alcohol (ALC). The predominant esters are, listed from greater to lower concentration in the oil: 13-docosenyl eicosenoate (C20:1 FA/C22:1 ALC), 11-eicosenyl eicosenoate (C20:1 FA/C20:1 ALC), 11-eicosenyl docosenoate (C22:1 FA/C20:1 ALC), 15-tetracosenyl eicosenoate (C20:1 FA/C24:1 ALC), 11-eicosenyl oleate (C18:1 FA/C20:1), and 13-docosenyl oleate (C18:1 FA/C22:1). Other esters which have been identified in lower concentrations include 13-docosenyl docosenoate (C22:1 FA/C22:1), 11-eicosenyl tetracosenoate (C24:1 FA/C20:1), octadecenyl eicosenoate (C20:1 FA/C18:1), 11-eicosenyl palmitate (C16:0 FA/C20:1), eicosanyl tetracosenoate (C24:1 FA/C20:0), eicosanyl palmitoleate (C16:1 FA/C20:0), 13-docosenyl palmitoleate (C16:1 FA/C22:1), and octadecenyl stearate (C18:0 FA/C18:1).

The reaction is preferably conducted using the jojoba seed oil, thereby obviating the need to separate the wax esters therefrom. Although the wax esters are present as an impure mixture in the oil, the other components of the oil (e.g., sterols and free fatty acids and alcohols) do not interfere with the reaction or significantly affect the physical properties of the dimerized oil produced. However, for reactions requiring a high degree of purity is understood that the reaction may be performed using only the wax esters from the oil.

In accordance with the process of this invention, the jojoba oil wax esters are reacted under conditions and for a period of time effective to at least partially, but preferably completely, produce dimers thereof. The reaction is conducted in the presence of a catalytically effective amount of an acid catalyst. A variety of acid catalysts are suitable for use herein, and include but are not limited to Lewis acids or strong protonic acids. Exemplary Lewis acids include $BF_3$, $BF_3$ etherate and $SbCl_5$, while exemplary strong protonic acids include sulfuric, trifluoroacetic, fluorosulfonic, and trifluoromethanesulfonic acids. $BF_3$ is preferred. The amount of the catalyst may vary somewhat with the particular catalyst selected, although even small amounts are effective. Without being limited thereto, typically the catalyst will be added at a concentration between about 1 to 5%, by weight, preferably between about 2 to 5%. The reaction is also conducted in a supercritical $CO_2$ medium as a solvent. The reaction should be carried out at a temperature and pressure above the critical temperature and pressure for $CO_2$. Thus, the temperature of the reaction should be above 31.1° C., and the pressure should be above 73.8 bar. However, the temperature is preferably between about 100-140° C., and the pressure is preferably 1400-1600 psi. Not only does the supercritical $CO_2$ provide an excellent solvent for the jojoba oil, but it is also environmentally friendly, inexpensive and non-flammable. The reaction time may vary with the temperature and catalyst concentration, and the reaction typically reaches completion in approximately 8-24 hours. After completion of the reaction, the dimerized oil product may be recovered. If desired, it is also envisioned that the dimerized esters may be separated from the remaining components of the oil by crystallization using petroleum ether. The reaction is preferably conducted under conditions which do not substantially (less than 5% by weight) hydrolyze or transesterify the wax esters. Thus, strong acid or alkali conditions are avoided, with a pH of the reaction preferably approximately pH neutral, between 6-8, and alcohols such as ethanol are not added.

The dimerization of the jojoba esters occurs in a single step, with the double bonds of the wax esters opening and cross linking or polymerizing two of the esters as dimers. Surprisingly, the cross linking occurs between the double bonds of the alcohol components of the jojoba esters, while the double bonds of the fatty acid components remain unreacted. Thus, the oligomerization of the jojoba oil produces dimers without the formation of trimers or higher polymers. The dimerized jojoba oil product possesses surprising physical properties which render it ideal for use in cosmetic and pharmaceutical and/or dermatological products; the dimerized oil is a solid at room temperature, with a melting point between 37-38° C. which is approximately the temperature of the human body.

The dimerization reaction of this invention between two of the same or different jojoba oil esters (2) and (2') may be shown by the following formula:

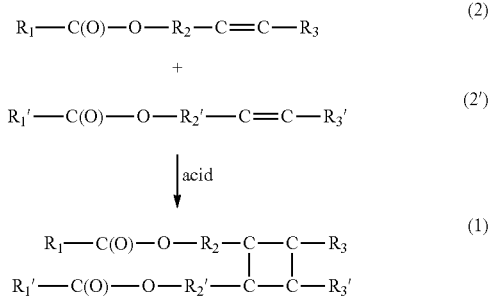

wherein $R_1$ and $R_1'$ are independently selected from the group of C15-C23 (straight chain alkenyl) monounsaturated hydrocarbons, $R_2$ and $R_2'$ are independently selected from the group of C8-C14 saturated (aliphatic) hydrocarbons, and $R_3$ and $R_3'$ are independently selected from the group of C6-C8 saturated (aliphatic) hydrocarbons.

As noted above, the composition of the wax esters of jojoba oil has been described by Busson-Breysse et al. (ibid) and Miwa (ibid). Using the formula above, the wax ester fraction of jojoba oil includes the following esters of a fatty acid with an alcohol:

| Acid/Alcohol | | $R_1$ | $R_2$ | $R_3$ |
|---|---|---|---|---|
| C20:1/C22:1 | 13-Docosenyl eicosenoate 41.4 | 19 | 12 | 8 |
| C20:1/C20:1 | 11-Eicosenyl eicosenoate 28.0 | 19 | 10 | 8 |
| C22:1/C20:1 | 11-Eicosenyl docosenoate 10.3 | 21 | 10 | 8 |
| C20:1/C24:1 | 15-Tetracosenyl eicosenoate 6.8 | 19 | 14 | 8 |
| C18:1/C20:1 | 11-Eicosenyl oleate 5.7 | 17 | 10 | 8 |
| C18:1/C22:1 | 13-Docosenyl oleate 3.4 | 17 | 12 | 8 |
| C22:1/C22:1 | 13-Docosenyl docosenoate 1.9 | 21 | 12 | 8 |
| C24:1/C20:1 | 11-Eicosenyl tetracosenoate 0.9 | 23 | 10 | 8 |
| C20:1/C18:1 | 9- or 11-Octadecenyl eicosenoate 0.7 | 19 | 8 | 8 |
| | | | 10 | 6 |
| C16:0/C20:1 | 11-Eicosenyl palmitate 0.3 | 15 | 10 | 8 |
| C24:1/C20:0 | Eicosanyl tetracosenoate 0.2 | 23 | — | — |
| C16:1/C20:0 | Eicosanyl palmitoleate 0.1 | 15 | — | — |
| C16:1/C22:1 | 13-Docosenyl palmitoleate 0.1 | 15 | 12 | 8 |
| C18:0/C18:1 | 9- or 11-Octadecenyl stearate 0.1 | 17 | 8 | 8 |
| | | | 10 | 6 | wherein $R_2$, $R_2$ and $R_3$ are as used in formulas (1), (2) and (3). Each of these wax esters having an unsaturated alcohol component may form a dimer in accordance with this invention. However, owing to their prevalence in the oil, dimers wherein $R_1$ and $R_1'$ are independently selected from the group of C17:1, C19:1 and C21:1 monounsaturated hydrocarbons (i.e., the FA component comprises oleic acid, 11-eicosenoic acid or erucic acid, respectively), $R_2$ and $R_2'$ are independently selected from the group of C10, C12 and C14 saturated (aliphatic) hydrocarbons, and $R_3$ and $R_3'$ are a C8 saturated (aliphatic) hydrocarbon (i.e., the alcohol component comprises 11-eicosenol, 13-docosenol or 15-tetracosenol, respectively), will be predominant in the dimerized oil product. Of these dimers wherein $R_1$ and $R_1'$ are independently selected from the group of C19:1 and C21:1 monounsaturated hydrocarbons, $R_2$ and $R_2'$ are independently selected from the group of C10 and C12 saturated hydrocarbons, and $R_3$ and $R_3'$ are a C8 saturated hydrocarbon will be present in the greatest concentrations.

The dimerized wax esters of this invention have superior properties which render them useful as a base or carrier for formulating cosmetics and pharmaceutical and/or dermatological products. The dimerized esters may also be used as lubricants or nanolubricatants, or as non-caloric fat-free food additives or plasticizers.

It is understood that the foregoing detailed description is given merely by way of illustration and that modifications and variations may be made therein without departing from the spirit and scope of the invention.

We claim:

1. A composition comprising dimerized jojoba oil.

2. The composition of claim 1 wherein jojoba oil comprises wax esters of unsaturated fatty acids and unsaturated alcohols, and said dimerized jojoba oil comprises dimers of said wax esters.

3. The composition of claim 2 wherein said dimers are formed between the said unsaturated alcohols of said wax esters.

4. The composition of claim 3 which is produced by the reaction of jojoba oil wax esters in the presence of a catalytically effective amount of an acid catalyst in supercritical $CO_2$.

5. The composition of claim 3 wherein said dimers comprise the structure:

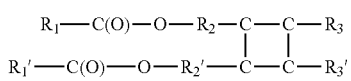

wherein $R_1$ and $R_1'$ are independently selected from the group consisting of C15-C23 monounsaturated hydrocarbons, $R_2$ and $R_2'$ are independently selected from the group consisting of C8-C14 saturated hydrocarbons, and $R_3$ and $R_3'$ are independently selected from the group consisting of C6-C8 saturated hydrocarbons.

6. The composition of claim 5 wherein said $R_1$ and $R_1'$ are independently selected from the group consisting of C17:1, C19:1 and C21:1 monounsaturated hydrocarbons, $R_2$ and $R_2'$ are independently selected from the group consisting of C10, C12 and C14 saturated hydrocarbons, and $R_3$ and $R_3'$ are a C8 saturated hydrocarbon.

7. The composition of claim 5 wherein said $R_1$ and $R_1'$ are independently selected from the group consisting of C19:1 and C21:1 monounsaturated hydrocarbons, $R_2$ and $R_2'$ are independently selected from the group consisting of C10 and C12 saturated hydrocarbons, and $R_3$ and $R_3'$ are a C8 saturated hydrocarbon.

8. A compound comprising a dimerized wax ester of jojoba oil of the structure:

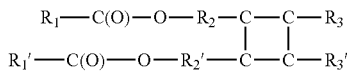

wherein $R_1$ and $R_1'$ are independently selected from the group consisting of C15-C23 monounsaturated hydrocarbons, $R_2$ and $R_2'$ are independently selected from the group consisting of C8-C14 saturated hydrocarbons, and $R_3$ and $R_3'$ are independently selected from the group consisting of C6-C8 saturated hydrocarbons.

9. The compound of claim 8 wherein said $R_1$ and $R_1'$ are independently selected from the group consisting of C17:1, C19:1 and C21:1 monounsaturated hydrocarbons, $R_2$ and $R_2'$ are independently selected from the group consisting of C10, C12 and C14 saturated hydrocarbons, and $R_3$ and $R_3'$ are a C8 saturated hydrocarbon.

10. The compound of claim 8 wherein said $R_1$ and $R_1'$ are independently selected from the group consisting of C19:1 and C21:1 monounsaturated hydrocarbons, $R_2$ and $R_2'$ are independently selected from the group consisting of C10 and C12 saturated hydrocarbons, and $R_3$ and $R_3'$ are a C8 saturated hydrocarbon.

11. A method for making dimerized jojoba oil comprising reacting jojoba oil wax esters in the presence of a catalytically effective amount of an acid catalyst in supercritical $CO_2$.

12. The method of claim 11 wherein jojoba oil comprises wax esters of unsaturated fatty acids and unsaturated alcohols, and said dimerized jojoba oil comprises dimers of said wax esters.

13. The method of claim 12 wherein said dimers are formed between said unsaturated alcohols of said wax esters.

14. The method of claim 12 further comprising recovering the reaction product comprising said dimers.

15. The method of claim 12 wherein said dimers are of the structure:

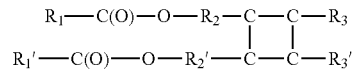

wherein $R_1$ and $R_1'$ are independently selected from the group consisting of C15-C23 monounsaturated hydrocarbons, $R_2$ and $R_2'$ are independently selected from the group consisting of C8-C14 saturated hydrocarbons, and $R_3$ and $R_3'$ are independently selected from the group consisting of C6-C8 saturated hydrocarbons.

16. The method of claim 15 wherein said $R_1$ and $R_1'$ are independently selected from the group consisting of C17:1, C19:1 and C21:1 monounsaturated hydrocarbons, $R_2$ and $R_2'$ are independently selected from the group consisting of C10, C12 and C14 saturated hydrocarbons, and $R_3$ and $R_3'$ are a C8 saturated hydrocarbon.

17. The method of claim 15 wherein said $R_1$ and $R_1'$ are independently selected from the group consisting of C19:1 and C21:1 monounsaturated hydrocarbons, $R_2$ and $R_2'$ are independently selected from the group consisting of C10 and C12 saturated hydrocarbons, and $R_3$ and $R_3'$ are a C8 saturated hydrocarbon.

18. The method of claim 12 wherein said reacting is under conditions which do not substantially hydrolyze said wax esters.

* * * * *